United States Patent
Sprunck et al.

(10) Patent No.: US 6,794,559 B2
(45) Date of Patent: Sep. 21, 2004

(54) PROMOTERS FOR GENE EXPRESSION IN CARYOPSES OF PLANTS

(75) Inventors: Stefanie Sprunck, Hamburg (DE); Antje Kluth, Hamburg (DE); Dirk Becker, Hamburg (DE); Stephanie Luetticke, Hamburg (DE); Horst Loerz, Hamburg (DE)

(73) Assignee: Bayer CropScience GmbH, Frankfurt am Main (DE)

( * ) Notice: Subject to any disclaimer, the term of this patent is extended or adjusted under 35 U.S.C. 154(b) by 0 days.

(21) Appl. No.: 09/899,595

(22) Filed: Jul. 5, 2001

(65) Prior Publication Data

US 2003/0018994 A1 Jan. 23, 2003

(30) Foreign Application Priority Data

Jul. 6, 2000 (DE) .......................... 100 32 379

(51) Int. Cl.⁷ .................. C12N 15/00; C12N 15/11; C12N 15/82; A01H 5/00; A01H 5/02
(52) U.S. Cl. .................. 800/287; 800/278; 800/298; 435/252.3; 435/254.11; 435/320.1; 435/419; 536/23.1; 536/24.1
(58) Field of Search .................. 435/254.11, 252.3, 435/410, 468, 320.1, 419; 800/278, 295, 298, 287; 536/23.1, 24.1

(56) References Cited

FOREIGN PATENT DOCUMENTS

WO    WO 97/45545    12/1997

OTHER PUBLICATIONS

Park Y. D. et al., Plant Journal Feb. 9, 1996, (2): pp. 183–194.*
Benfey et al., Science 250:959–966, 1990.*
Ellis J. et al., EMBO Journal, 1987, vol. 6, No. 1, pp. 11–16.*
Matsuoka M. et al., Plant Journal, 1994, vol. 6, No. 3 pp. 311–319.*
Robert L. et al., Plant Cell, Dec. 1989, vol. 1, pp. 569–578.*
Li Z., et al. Plant Physiology, Aug. 1999, vol. 120, pp. 1147–1155.*
Rohde et al, "Structural Analysis of the *Waxy* Locus from *Hordeum vulgare*", Nucleic Acids Research, vol. 16, No.14, 1988, Accession Nos. X07931, X07932.
Klösgen et al, "Molecular Analysis of the *Waxy* Locus of *Zeas mays*", Mol. Gen. Genet. (1986), pp. 203–237.
Lennart Walter, 2000, PhD. Thesis, University of Hamburg, School of Biology, Untersuchungen zur Expression und Funktion der Stärkesynthasell (SSII) aus Weizen (*Triticum aestivm L.*).
EMBL Database Accession No. TAU66377.
Li et al, "The Localization and Expression of the Class II Starch Synthases of Wheat", Plant Physiology, 1999, vol. 120, pp. 1147–1155.
Gao et al, Isolation, Characterization, and Expression Analysis of Starch Synthase IIa cDNA from Wheat (*Triticum Aestivum L.*), Genome 43, 2000, 768–775.

* cited by examiner

*Primary Examiner*—Ashwin D. Mehta
*Assistant Examiner*—Russell Kallis
(74) *Attorney, Agent, or Firm*—Frommer Lawrence & Haug LLP

(57) ABSTRACT

The present invention provides promoters which bring about a caryopsis-specific expression of coding nucleotide sequences controlled by them, and to expression cassettes, recombinant vectors and host cells containing such promoters. Transformed transgenic plant cells and plants and methods for generating them, are also described.

12 Claims, No Drawings

PROMOTERS FOR GENE EXPRESSION IN CARYOPSES OF PLANTS

The present invention relates to promoters which permit a caryopsis-specific expression or suppression of genes in genetically modified plants, to methods for the tissue-specific gene expression or gene suppression in plants, expression cassettes, recombinant vectors and host cells containing such promoters, to transgenic plant cells and plants transformed with said promoters, and to methods for generating such plant cells and plants.

Prior-art documents whose disclosure is herewith incorporated into the present application by reference are cited hereinbelow.

The application of plants whose genetic material has been modified with the aid of genetic engineering methods has proved advantageous in many fields of agriculture in order to transfer certain characteristics to crop plants. The predominant aims are firstly crop protection, and secondly improved quality and yield of the plants or products which can be harvested.

A large number of methods for genetically modifying dicotyledonous and monocotyledonous plants are known (cf., inter alia, Gasser and Fraley, Science 244 (1989), 1293–1299; Potrykus, Ann. Rev. Plant Mol. Biol. Plant Physiol. 42 (1991), 205–225; Newell, Mol. Biotechnol. 16(1), (2000), 53–65). They are frequently based on the transfer of gene constructs which, in most cases, constitute combinations of specific coding regions of structural genes with promoter regions and transcription terminators of the same or other (for example heterologous) structural genes.

In connection with the expression of structural genes, providing promoters is of great importance for generating transgenic plants, since the specificity of a promoter is decisive for the point in time at which, the tissue types in which, the physiological conditions under which and the intensity with which a transferred gene is expressed in the modified plant.

To succeed with these various approaches for the genetic manipulation of plants, it is therefore necessary to place genes to be regulated differently under the control of suitable promoters.

Transcriptional initiation and regulation is subject to the DNA segment of a gene termed promoter. As a rule, promoter sequences are in the 5'-flanking region of a transcribed gene. Individual elements of a promoter (for example transcriptional enhancers) can also be located in the 3'-flanking region or within intron sequences (Kuhlemeier, Plant Mol. Biol. 19 (1992): 1–14; Luehrsen, The Maize Handbook, 636–638) (1994).

The controlled expression of transgenes is very useful, for example for introducing resistance properties or the modification of metabolic processes in plants. If a transgene or its gene product is to engage into defined metabolic pathways of a plant, for example if it is to produce a new constituent or to protect from attack by pathogens, its spatially and/or temporarily controlled expression is only possible when an inducible and/or tissue- and/or development-specific promoter is used. Only this makes possible the specific production of desired constituents at a defined developmental stage or within a certain tissue of the plant. For example, when applying antisense technology, where the expression of plant-homologous genes is to be prevented, the use of tissue- and/or development-specific promoters is advantageous over a tissue- and/or developmental-independent expression when, for example, the antisense effect occurs precisely at the developmental stage, or precisely in the tissue, of the plant at which, or in which, the plant-homologous gene is also expressed.

A large number of promoters capable of governing the expression of transferred genes or structural genes in plants is already known. The most frequently used promoter is the 35S CaMV promoter (Franck et al., Cell 1 (1980), 285–294), which leads to constitutive expression of the gene introduced.

Frequently, inducible promoters are also employed, for example for wound induction (DE-A-3843628), chemical induction (Ward et al., Plant Molec. Biol. 22 (1993), 361–366) or light induction (Fluhr et al., Science 232 (1986), 1106–1112).

Under certain circumstances, the use of the frequently described constitutive promoters (e.g. 35 S) entails certain disadvantages. Promoters which bring about a constitutive expression of the genes controlled by them can be employed, for example, for generating herbicide-tolerant and pathogen-resistant plants, but have the disadvantage that the products of the genes controlled by them are present in all parts of the plant, which may be undesirable, for example when the plants are intended for consumption. A negative aspect of tissue- and/or development-independent expression of a transgene can also be an undesired effect on plant development. The use of inducible promoters likewise entails disadvantages, since the induction conditions are typically difficult to control in the open in the case of agricultural plants.

The use of cell- and tissue-specific promoters has also been described: stomata-specific gene expression (DE-A-4207358), seed-, tuber- and fruit-specific gene expression (reviewed in Edwards and Coruzzi, Annu. Rev. Genet. 24 (1990), 275–303; DE-A-3843627), phloem-specific gene expression (Schmülling et al., Plant Cell 1 (1989), 665–670), root-nodule-specific gene expression (DE-A-3702497) or meristem-specific gene expression (Ito et al., Plant Mol. Biol. 24 (1994), 863–878).

A limited number of promoters which regulate gene expression in the caryopsis are known as yet. The management of certain approaches in the genetic modification of plants therefore requires the provision of alternative promoter systems for gene expression in the caryopsis whose regulation differs from that of the known systems.

Starch biosynthesis genes whose gene products are expressed specifically in the storage tissue of the caryopsis, but not in vegetative tissues, have been isolated from various plant species, for example the relevant genes or cDNA clones of GBSS I. They include the waxy locus from maize (Klögen et al. (1986) Mol. Gen. Genet. 203: 237–244), and barley (Rohde et al. (1988) Nucleic Acid Research 16, 14: 7185–7186), rice (Wang et al. (1990) Nucleic Acid Research 18: 5898), potato (van der Leij et al. (1991) Mol. Gen. Genet. 228: 240–248), pea (Dry et al. (1992) Plant J. 2: 193–202), cassava (Salehuzzaman et al. (1993) Plant Mol. Biol. 20: 947–962), millet (Hsingh et al. (1995) EMBL Database Acc.No. U23954) and sugar beet (Schneider et al. (1999) Mol. Gen. Genet. 262: 515–524).

The gene products which are expressed specifically in the caryopsis also include type II starch synthase (SSII). Corresponding genes were isolated from maize (zSSIIa and zSSIIb; Ham et al. (1998) Plant Mol. Biol. 37: 639–649), pea (Dry et al. (1992) Plant J. 2: 193–202), potato (Edwards et al. (1995) Plant J. 8: 283–294) and sweet potato (Ham et al. (1998) Acc. Nr. AF068834).

The situation for wheat is as follows: cDNA clones both for the waxy gene and for the SSII gee were isolated and sequenced. In total, 3 different GBSSI cDNA clones were isolated from wheat (Clark et al. (1991) Plant Mol. Biol. 16: 1099–1101; Ainsworth et al. (1993) Plant Mol. Biol. 22: 67–82 (Block (1997) "Isolierung, Charakterisierung und Expressionsanalysen von Stärkesynthase-Genen aus Weizen" [Isolation, characterization and expression analyses of wheat starch synthase genes] (*Triticum aestivum* L.), PhD thesis, University of Hamburg).

In addition, coding sequences of a type II starch synthase (SSII) have also been isolated from a caryopsis-specific cDNA library, and their caryopsis-specific expression has been detected. Northern analyses have demonstrated that the transcripts of GBSS I (Block (1997), PhD thesis, University of Hamburg, School of Biology) and of SSII (Walter (2000), PhD thesis, University of Hamburg, School of Biology), WO 97/45545, EMBL Database Acc. No. U66377) are found during early developmental stages of the caryopsis, but not in assimilating leaf tissue. In addition, transcripts were also demonstrated in the endosperm and the pericarp for SSII.

Three cDNA sequences of the wheat SSII (*T. aestivum* L. cv. "Wyuna"; wSSII-A1, wSSII-B1, wSSII-D1) were furthermore isolated from an endosperm-specific cDNA library (Li et al., (1999) Plant Phys. 120: 1147–1155). Using PCR analyses, each of the three clones was assigned one genome of hexaploid wheat. Western blot analyses have demonstrated that the 100 kDa protein (SGP-B1) is present both in starch-granule-bound foam and in soluble foams during early stages of endosperm development. The isolation and characterization of 3 further SSII cDNA clones (*Triticum aestivum* L. cv. "Fielder", Ss2a-1, Ss2a-2, Ss2a-3) have been described since (Gao & Chibbar (2000) Genome 43: 768–775).

A cDNA clone of a starch-globule-band type II starch synthase (GBSS II) which is expressed not in the endosperm but only in the leaves and the pericarp of wheat has recently been isolated (Vrinten & Nakamura (2000) Plant Physiol.122: 255–263). In diploid wheat (*Triticum monococcum* L.), a 56 kDa isoform of a GBSS has also been described at the protein level (Fujita & Taira (1998) Planta 207: 125–132). This isoform can be detected in the pericarp, the aleuron and the embryo of immature caryopses.

While three homologous waxy structural genes positioned on chromosomes 7A, 4A and 7D of hexaploid wheat have been isolated in the meantime (Murai et al. (1999) Gene 234: 71–79), the promoter sequences of these or other genomic clones from wheat remain unknown. Only the 5'-flanking regions of GBSS I from barley (GenBank Acc.No. X07931), antirrhinum (GenBank Acc.No. AJ006294), rice (GenBank Acc.No. AB008794, AB008795), potato (GenBank Acc.No. X58453) and maize (GenBank Acc.No. X03935) are known.

If complex tasks in connection with the expression of genes in genetically modified organisms are to be tackled, it is therefore necessary to have a choice between different promoter systems which differ with regard to their specificity. The present invention makes a contribution here.

The aim of the present invention is thus to provide means for making possible a targeted caryopsis-specific gene expression in genetically modified plants, preferably in monocots.

The use of the means according to the invention, i.e. the nucleic acid molecules, vectors, cells or plants according to the invention, makes it possible to engage, in a tissue- and/or development-specifically defined manner, in the plant's metabolism, for example in the biosynthesis of storage starch, storage fats or storage proteins or else the utilization of the caryopsis as storage or synthesis organ for reserve materials (for example polyglucans, starch, fatty acids, fats, modified or unmodified storage proteins or biopolymers).

Thus, genes can be expressed specifically and at an early point in time in the caryopsis under the control of the nucleic acid molecules or promoter sequences according to the invention, in particular during the grain development of cereals.

Moreover, genes can be suppressed specifically and at an early point of the development in the caryopsis by what are known as "gene-silencing" strategies (cosuppression) by means of the promoter sequences according to the invention, in particular during the grain development of cereals. Cosuppression strategies using promoters have been described in detail by Vaucheret et al. (Vaucheret et al., 1998, 16(6), 651–659). The section "Transcriptional transinactivation" on page 652 of the paper by Vaucheret et al., which specifically describes cosuppression strategies for which the promoters according to the invention are suitable, in particular those which can be termed "ectopic transinactivation" therein (Matzke et al., 1994, Mol. Gen. Genet. 244, 219–229), be herewith incorporated into the present application by reference. Thus, the promoters according to the invention can be used to suppress gene expression of any genes which are under the control of a promoter which is accessible as target for cosuppression by the promoters according to the invention. If appropriate, even a sequence segment of as little as approximately 90 bp in length suffices for this purpose.

The promoters according to the invention thus make possible the targeted modifications of storage starch. Moreover, to make possible the widest possible application of starch for a very wide range of industrial requirements, it is desirable to provide plants which synthesize starches with defined properties. Thus, decisive properties such as solubility, gelatinization behavior, tendency to undergo retrogradation, viscosity and complex formation are determined by the amylose/amylopectin ratio, the degree of branching of the amylopectin and the derivatization of the polymers. A targeted modification of such properties replaces complicated methods for separating amylose and amylopectin or the expensive chemical modification of starch.

A limited possibility of obtaining plants with modified storage starch is the application of traditional plant breeding methods. An (amylose-free) "waxy" wheat was generated successfully by hybridizing spontaneously occurring mutants (Nakamura et al. (1995) Mol. Gen. Genet. 248: 253–259). According to the polyploid character of the commercially important aestivum wheat, mutations relating to the starch structure are not easily recognized since they are compensated for by intact alleles. Thus, the application of traditional plant breeding methods is difficult. Moreover, only enzyme activities which already exist can be resorted to. Novel activities which have hitherto not been identified in plants or which have been identified in plants (or other organisms) which cannot be hybridized with the target plant can also not be improved with the aid of plant breeding methods.

An alternative to traditional plant breeding methods is the targeted modification of starch-producing plants by genetic engineering methods. However, prerequisite herefor is, besides the identification and isolation of genes whose gene products are involved in starch synthesis and/or of starch modification, the use of specific promoters which may be a tissue- and/or development-specific expression of the genes controlled by them in the starch-forming tissues.

Employing the promoter sequences according to the invention also additionally makes possible the integration into the plant genome of genes which impart, to the cereal endosperm, a modified function as storage tissue, for example for storing storage materials other than starches.

These aims are achieved in accordance with the invention by the use forms characterized in the patent claims.

It has been found within the scope of the present invention that a promoter as defined hereinbelow surprisingly brings about, in plants, a caryopsis-specific expression of a coding nucleotide sequence controlled by this promoter.

Thus, the present invention relates to a nucleic acid molecule with the function of a caryopsis-specific promoter, which nucleic acid molecule a) comprises the nucleic acid sequence defined by the nucleotides 1–4683 of Seq ID No. 1 and corresponding to the one deposited by DSM 14224 (plasmid p. 15/G);

b) comprises one or more sequence elements selected from the group consisting of
i) (Seq ID No. 2);
ii) (Seq ID No. 3);
iii) (Seq ID No. 4);
iv) (Seq ID No. 5);
v) (Seq ID No. 6);
vi) (Seq ID No. 7);
vii) (Seq ID No. 8);
viii) (Seq ID No. 9) and
ix) (Seq ID No. 10);

c) comprises a functional portion of the nucleic acid sequence stated under a);

d) comprises a sequence which hybridizes with at least one of the nucleic acid sequences stated under a) and/or b); and/or e) comprises a sequence which has at least 60% identity, preferably at least 75% identity, in particular at least 90% identity and very especially preferably at least 95% identity, with one of the nucleic acid sequences stated under a). SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10; and The subject matter of the present invention is furthermore a nucleic acid molecule with the function of a caryopsis-specific promoter which a) comprises one or more sequence elements selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10; and b) comprises a functional portion of Seq ID No.1, preferably one or more sequence elements from the group consisting of nucleotides of positions 1–72, 78–194, 200–402, 409–579, 588–734, 743–837, 852–865, 872–940, 948–957, 962–1113, 1120–1180, 1186–1218, 1227–1330, 1336–1538, 1545–1567, 1574–1589, 1597–2015, 2021–2043, 2052–2087, 2096–2276, 2292–2320, 2336–2352, 2361–2470, 2478–2531, 2540–2602, 2609–2712, 2721–2786, 2794–2870, 2883–2937, 2943–2979, 2986–3048, 3056–3073, 3080–3098, 3106–3133, 3142–3155, 3163–3197, 3205–3289, 3302, 3311–3317, 3318–3405, 3414–3446, 3453–3533, 3541–3570, 3578–3617 3617, 3625–3750, 3757–3978, 3988–4031, 4038–4109, 4116–4145, 4153–4173, 4180–4294, 4301–4419, 4427–4449, 4456–4466, 4474–4480, 4489–4683 of Seq. ID No. 1.

The terms "nucleic acid molecule according to the invention" and "promoter according to the invention" are used synonymously for the purposes of the present invention.

In a preferred embodiment, the promoters according to the invention are those of plant genes, preferably monocots, or derived from such genes. In a further preferred embodiment, the promoters according to the invention are suitable for expressing or suppressing genes in genetically modified organisms, preferably in genetically modified plants, algae or yeasts, especially in genetically modified monocots, and in particular for the expression or suppression of starch synthase genes in said genetically modified organisms. In this context, the promoters according to the invention can be derived from plant genes, obtained from algae or yeasts, modified by recombinant DNA techniques and/or generated synthetically.

The promoters according to the invention can be modified for example by being combined with further cis-regulatory elements. Thus, the promoters according to the invention can additionally be combined with enhancer elements in order to enhance the expression of the corresponding nucleic acid molecule without however influencing its tissue-specific expression. Individual cis-elements (see below) of the isolated promoters can also be combined with each other to give regulatory units.

A measure for the promoter activity is, for example, the expression rate determined for a particular marker gene which is under the regulatory control of the promoter according to the invention. Examples of suitable marker genes are the *E. coli* β-glucuronidase gene (gus) (Jefferson (1987) Plant Molecular Biology Reporter Vol. 5 (4): 387–405) or the green fluorescence protein gene (gfp) (Baulcombe et al., Plant J. 7 (16) (1993), 1045–1053). The organ or tissue specificity can be determined readily by comparison of the expression rates for said marker genes determined from individual tissues or organs of the plant. Functional portions of the promoter sequence according to the invention comprise, for the purposes of the present invention, naturally occurring variants and also artificial nucleotide sequences, for example those obtained by mutagenesis or chemical synthesis.

In the context of the present invention, a "promoter" is to be understood as meaning a DNA sequence comprising the regulatory portion of a gene, preferably a structural gene. "Regulatory portion" of a gene is to be understood as meaning that portion that determines the expression conditions of the gene. The regulatory portion has sequence motifs with which transcriptional factors and RNA polymerase(s) interact and initiate transcription of the coding portion of the gene. In addition, the regulatory portion can comprise one or more positive regulatory elements, known as 'enhancers'. Additionally or instead, however, it may also comprise negatively regulatory elements, known as 'silencers'. A "structural gene" is generally to be understood as meaning a genetic unit of regulatory and coding portions whose gene product is generally a protein. The information for the primary amino acid sequence of the gene product is present in the coding portion of the structural gene, while the regulatory portion determines when, in what tissues, under what physiological conditions and in what quantities the transcript of the coding portion is formed according to whose template the gene product is synthesized.

The term "caryopsis-specific" is to be understood as meaning, for the purposes of the present invention, that a gene under the control of a promoter according to the invention is expressed in the caryopsis, i.e. endosperm, pericarp, aleuron, embryo and/or scutellum, preferably at an early point in time, i.e. earlier than 15 dap (dap=days after pollination), preferably earlier than 10 dap, particularly preferably earlier than 6 dap. For the purposes of the present invention, a lower limit for the expression time of preferably 5 dap, particularly preferably 3 dap, in particular 2 dap and very particularly preferably 1 dap applies for said "early expression". In particular, caryopsis specificity for the purposes of the present invention exists when the promoter according to the invention favors the expression of a gene in the caryopsis, preferably in the central starch endosperm, over other tissues such as, for example, mature leaves or roots and brings about a significant increase in the caryopsis, i.e. expression which is increased by a factor of at least 2 to 5, preferably 5 to 10, in particular 10 to 100 or higher.

In the context of the present invention, caryopsis specificity can be analyzed for example by customary reporter gene experiments. To test an isolated promoter sequence for its promoter activity in the caryopsis, the promoter can, for example, be linked operably to a reporter gene, such as, for example, E. coli β-glucuronidase gene in an expression cassette or in a vector for plant transformation. This construct is then used for transforming plants. The expression of β-glucuronidase in the caryopsis is then determined in comparison with other tissues such as, for example, mature leaves or roots, for example as described by Martin et al. (The GUS Reporter System as a Tool to Study Plant Gene Expression, In: GUS Protocols: Using the GUS genes as a Reporter of Gene Expression, Academic Press (1992), 23–43).

The skilled worker is familiar with the term "caryopsis"; it comprises in particular pericarp and endosperm. Since these tissues undergo dynamic development, the development of the endosperm, for example, into various types of cells and tissues correlates with different biochemical activities, owing to differential gene expression. Additional reference may be made to Olsen et al. (Olsen et al., 1999, Trends in Plant Science 4 (7), 253–257).

The promoter according to the invention permits caryopsis-specific gene expression of a coding nucleotide sequence controlled by it. It constitutes an interesting alternative to known endosperm-specific promoters since it is active in the caryopsis at a very early point in time, i.e. <15 dap, preferably <10 dap, in particular <6 dap (dap=days after pollination). The promoter according to the invention allows in particular the expression of genes whose gene products are involved in the starch metabolism of monocots, in particular in wheat, to be governed efficiently.

The promoters according to the invention can moreover be used in many different ways. For example, they make possible the generation of transgenic plants which, owing to a modified metabolism in the caryopsis, show a qualitatively and/or quantitatively modified composition of reserves in their storage tissue, i.e. in the cereal grain.

Besides the promoter which exhibits the entire sequence defined by the nucleotides 1–4683 of Seq ID No. 1 or the sequence deposited accordingly by DSM 14224, the present invention also relates to promoters which exhibit a functional portion of this sequence and which, in plants, bring about a caryopsis-specific expression of a coding nucleotide sequence controlled by them.

A "functional portion" of the promoter according to the invention is to be understood as meaning, for the purposes of the present invention, those sequences which do not comprise the complete sequence of the promoter, as defined by nucleotide 1-4683 of Seq ID No. 1 or deposited by DSM 14224, but which are truncated. Despite the truncation, a "functional portion of the promoter according to the invention" has the caryopsis specificity according to the invention. Sequences comprising a functional portion of the promoter according to the invention of Seq. ID No. 1 preferably exhibit one or more of the segments from Seq ID No. 1 enumerated hereinbelow: 1–72, 78–194, 200–402, 409–579, 588–734, 743–837, 852–865, 872–940, 948–957, 962–1113, 1120–1180, 1186–1218, 1227–1330, 1336–1538, 1545–1567, 1574–1589, 1597–2015, 2021–2043, 2052–2087, 2096–2276, 2292–2320, 2336–2352, 2361–2470, 2478–2531, 2540–2602, 2609–2712, 2721–2786, 2794–2870, 2883–2937, 2943–2979, 2986–3048, 3056–3073, 3080–3098, 3106–3133, 3142–3155, 3163–3197, 3205–3289, 3302, 3311–3317, 3318–3405, 3414–3446, 3453–3533, 3541–3570, 3578–3617, 3625–3750, 3757–3978, 3988–4031, 4038–4109, 4116–4145, 4153–4173, 4180–4294, 4301–4419, 4427–4449, 4456–4466, 4474–4480, 4489–4683. The numbers given indicate the nucleotide positions in Seq. ID No. 1.

A "functional portion" of the promoter sequence according to the invention is to be understood as meaning in particular also natural or artificial mutations of an originally isolated promoter sequence which have the features according to the invention. The term "mutation" encompasses the substitution, addition, deletion, exchange and/or insertion of one or more nucleotides or nucleotide motifs, in particular of cis-elements (see below). The aim of such modifications can be, for example, the generation of fragments, the insertion or repositioning of known nucleotide motifs such as, for example, restriction cleavage sites or cis-elements. Thus, the scope of the present invention also extends for example to those nucleotide sequences which can be obtained by modifying the promoter sequence defined by the nucleotides 1–4683 of Seq ID No. 1 or the promoter sequence deposited by DSM 14224 and which have structural and functional features which are essential according to the invention.

"Functional portions" of the promoter sequence according to the invention in this context also comprise those promoter variants whose promoter activity is reduced or enhanced compared with the unmodified, that is to say naturally obtainable promoter (wild type).

In particular, a "functional portion" of the promoter sequences according to the invention are the regions identifiable by deletion analysis (cf. examples part), preferably the sequence segments 2241–4683; 2637–4683; 3569–4683; 4071–4683; 4151–4683 and 4403–4683 of Seq ID No. 1.

In principle, the activity of a eukaryotic RNA polymerase II promoter is caused by the synergistic action of various trans-active factors (DNA-binding molecules such as proteins or hormones) which bind to the various cis-regulatory DNA elements ('cis-elements') present in the promoter, generally DNA regions approximately 10–20 nucleotides in length. These factors interact directly or indirectly with individual or several factors of the basic transcription machinery, which eventually leads to the formation of a pre-initiation complex in the vicinity of the transcription start (Drapkin et al., Current Opinion in Cell Biology 5 (1993), 469–476). A module-light construction of the eukaryotic RNA polymerase II promoters can be assumed where the cis-elements (modules), as components of the promoter, specifically determine its activity (Tjian and Maniatis, Cell 77 (1994), 5–8).

Individual subdomains of the promoter according to the invention which potentially mediate tissue specificity can be identified for example by fusion with a minimal-promoter/reporter-gene-cassette. A minimal promoter is to be understood as meaning a DNA sequence comprising a TATA-box located approximately 20 to 30 base pairs upstream of the transcription start, or an initiator sequence (Smale and Baltimore, Cell 57 (1989), 103–113; Zawel and Reinberg, Proc. Natl. Acad. Sci. 44 (1993), 67–108; Conaway and Conaway, Annu. Rev. Biochem 62 (1993), 161–190). Examples of minimal promoters are the −63 to +8 Δ35S promoter (Frohberg, PhD thesis at the FU Berlin, School of Biology (1994)), the −332 to +14 minimal patatin class I promoter, and the −176 to +4 minimal PetE promoter (Pwee et al., Plant J. 3 (1993), 437–449).

Moreover, subdomains or cis-elements of the promoter according to the invention can also be identified via deletion analyses or mutageneses (Kawagoe et al., Plant J. 5(6) (1994), 885–890). The test for functionality of such a subdomain or cis-elements of the promoter can be effected in planta by detecting reporter gene activity in stably transformed cells.

In a further embodiment, the present invention therefore relates to modifications of Seq. ID No.1 obtained in particular by the di- or multimerization of subdomains or cis-elements of Seq ID No. 1, in particualr the nucleotide sequence 1-4683 of Seq. ID No.1.

In a further embodiment of the invention, an increased promoter activity compared with the wildtype is achieved by combining the promoter according to the invention with one or more 'enhancers'.

Various enhancer elements have been described in the literature, all of which generally bring about an increase in the expression in a tissue-specific manner, the tissue specificity generally being determined by the particular enhancer used (Benfey et al., Science 250 (1990), 959–966; Benfey et al., EMBO J. 8 (1989), 2195–2202; Chen et al., EMBO J. 7, (1988), 297–302; Simpson et al., Nature 323 (1986), 551–554).

In addition, there are also enhancer elements such as, for example, the PetE enhancer (Sandhu et al., Plant Mol. Biol. 37 (1998), 885–896), which do not act in a tissue-specific manner and which can therefore be placed before the promoter according to the invention as quantitative enhancer elements in order to increase the expression rate of the controlled gene in the caryopsis without modifying the tissue specificity of the promoter according to the invention.

Furthermore, the synthetic enhancer elements known to the person skilled in the art can also be used; these are, for example, derived from naturally occurring enhancers and/or are obtained by combining enhancer elements.

Likewise, the present invention also relates to promoters which exhibit a nucleotide sequence which hybridizes with the nucleotide sequence defined by the nucleotides 1–4683 of Seq ID No. 1 or deposited by DSM 14224, preferably under stringent conditions, and which promoters exert, in plants, a caryopsis-specific effect on the expression of a coding nucleotide sequence controlled by them.

In this context, the term "stringent conditions" means for example hybridization conditions as they are described in Sambrook et al. (Molecular Cloning, A Laboratory Manual, 2nd Edition (1989), Cold Spring Harbor Laboratory Press, Cold Spring Harbor, N.Y.). In particular, stringent hybridization takes place under the following conditions:

Hybridization buffer: 2× SSC; 10× Denhardt's solution (Ficoll 400+PEG+BSA; ratio 1:1:1); 0.1% SDS; 5 mM EDTA; 50 mM $Na_2HPO_4$; 250 μg/ml herring sperm-DNA; 50 μg/ml tRNA; or 0.25 M sodium phosphate buffer pH 7.2, 1 mM EDTA, 7% SDS Hybridization temperature T=65 to 68° C.;

Wash buffer 0.2 × SSC; 0.1% SDS;

Wash temperature T=65 to 68° C.

Such promoters preferably have a sequence identity of at least 30%, especifically preferably of at least 40%, very preferably of at least 50%, especially preferably of at least 60%, particularly preferably of at least 70%, very particularly preferably of at least 80%, very particularly especially preferably at least 90% and in particular very particularly especially preferably at least 95%, with the nucleotides 1–4683 of Seq ID No. 1 or functional portions according to the invention thereof.

The degree of identity of sequences with the promoter according to the invention can be determined by customary sequence alignment with nucleotides 1–4683 of Seq ID No. 1.

When two sequences to be compared differ in length, the sequence identity preferably refers to the percentage of the nucleotide residues of the shorter sequence, which are identical to the nucleotide residues of the longer sequence. The sequence identity can usually be determined by using computer programs such as, for example, the Bestfit program (Wisconsin Sequence Analysis Package, Version 8 for Unix, Genetics Computer Group, University Research Park, 575 Science Drive Madison, Wis. 53711). Bestfit exploits the local homology algorithm of Smith and Waterman, Advances in Applied Mathematics 2 (1981), 482–489, to determine the segment with the highest sequence identity. When applying Bestfit or another sequence alignment program to determine whether a particular sequence has, for example, 95% identity with a reference sequence of the present invention, the parameters are preferably set in such a way that the percentage identity over the entire length of the reference sequence is calculated and that homology gaps of up to 5% of the total number of nucleotides in the reference sequence are permitted. When using Bestfit, the so-called optional parameters can be left at their default values. The deviations which occur when comparing a given sequence with the above-described sequences of the invention can have been caused for example by addition, deletion, substitution, insertion or recombination. Promoter sequences which, as described above, hybridize with nucleotides 1–4683 of Seq ID No. 1 or the corresponding nucleotides sequence deposited by DSM 14224 are preferably derived from plant organisms, preferably from higher plants, especially preferably from monocots, particularly preferably from Gramineae, very especially from plants of the genus Triticum.

Furthermore, the present invention also relates to promoters which exhibit a functional portion of these sequences and which, in plants, bring about a caryopsis-specific expression of a coding nucleotide sequence controlled by them and which comprise one or more sequences selected from the group comprising the nucleotides 1–4683 of Seq ID No. 1, Seq ID No. 2, Seq ID No. 3, Seq ID No. 3, Seq ID No. 4, Seq ID No. 5, Seq ID No. 6, Seq ID No. 7, Seq ID No. 8, Seq ID No. 9 and Seq ID No. 10.

The present invention furthermore relates to expression cassettes comprising one or more promoters according to the invention. In this context, the term "expression cassette" is to be understood as meaning the combination of a promoter according to the invention with a nucleic acid sequence to be expressed. This nucleic acid sequence can be, for example, a polypeptide-encoding sequence, for example a gene which can be linked to the promoter in sense or antisense orientation. The nucleic acid sequence can also code a nontranslatable RNA, for example an antisense RNA or a ribozyme. These nucleic acid sequences can be used in conjunction with the promoter according to the invention to generate plants with a modified phenotype.

Furthermore, the expression cassettes according to the invention can comprise a transcription termination sequence downstream of the 3' end of the nucleic acid sequence which is linked to the promoter. In this context, a "transcription termination sequence" is to be understood as meaning a DNA sequence which is located at the 3' end of a coding gene segment and which is capable of bringing about transcription termination and, if appropriate, the synthesis of a poly-A-tail. An example of such a termination sequence is that of the octopine synthase gene. The skilled worker is familiar with others.

Moreover, the present invention relates to a vector comprising one or more promoters or expression cassettes according to the invention.

In an embodiment which is furthermore preferred, the promoter in the vector according to the invention is linked to restriction cleavage sites or a polylinker, either of which permits integration of any sequences downstream of the promoter. In this context, a "polylinker" is to be understood as meaning a DNA sequence containing recognition sequences of at least one restriction enzyme, preferably of 5 or more restriction enzymes.

In an especially preferred embodiment, a vector according to the invention additionally comprises a sequence for transcription termination, for example that of the octopine synthase gene, downstream of the promoter or the polylinker.

Thus, the present invention likewise relates to vectors comprising one or more expression cassettes according to the invention. If appropriate, the vectors according to the invention comprise selection markers which are suitable for readily identifying, and, if appropriate, selecting cells comprising the vectors according to the invention following transformation.

In a preferred embodiment, the vectors according to the invention are suitable for transforming plant cells, especially preferably for integrating foreign DNA (for example transgenes) into the plant genome. An example of such vectors are binary vectors, some of which are commercially available.

The present invention furthermore relates to host cells which are genetically modified with a nucleic acid molecule according to the invention, or promoter according to the invention, an expression cassette according to the invention or a vector according to the invention, in particular plant cells or microbial cells, for example of the genus Agrobacterium.

In this context, "genetically modified" means that the host cell comprises a promoter according to the invention, an expression cassette according to the invention or a vector according to the invention, preferably stably integrated into the genome of the host cell, and that the promoter, or the expression cassette, has been introduced as foreign DNA into the host cell or beforehand into a precursor of this cell. The host cells according to the invention can therefore be themselves the immediate product of a transformation for the purposes of the present invention or be derived from such cells which comprise a promoter according to the invention or an expression cassette according to the invention. Suitable host cells are prokaryotic cells, in particular bacterial cells, or else eukaryotic cells. Eukaryotic cells can be of plant origin, but also derived from fungi, in particular from the genus Saccharomyces.

In a further embodiment, the invention relates to the use of vectors according to the invention, expression cassettes according to the invention or host cells according to the invention, in particular of the genus Agrobacterium, for transforming plants, plant cells, plant tissues or plant parts.

In an especially preferred embodiment, the host cells according to the invention are plant cells, termed "transgenic plant cells" hereinbelow.

Furthermore, the present invention also relates to plants comprising plant cells according to the invention. In principle, these plants may belong to any plant species, plant genus, plant family, plant order or plant class which is commercially utilizable. They may be monocots or else dicots. The plants according to the invention are preferably useful plants, i.e. plants which are of agricultural, silvicultural and/or horticultural interest. Preferred in this context are agricultural useful plants, in particular cereal species such as, for example, wheat, oats, barley, rye, maize, rice, fodder and forage grasses (such as, for example alfalfa, white clover or red clover), in particular wheat.

In a further embodiment, the present invention also relates to methods for generating transgenic plant cells and plants, which comprises transforming plant cells, plant tissues, plant parts or protoplasts with a nucleic acid molecule according to the invention, a vector according to the invention, an expression cassette according to the invention or, if appropriate, with a host cell according to the invention, preferably a microorganism, growing the transformed cells, tissues, plant parts or protoplasts in a growth medium, and, when transgenic plants are generated, regenerating plants from these.

In a further embodiment, the invention relates to the use of vectors, expression cassettes or, if appropriate, host cells according to the invention for generating transgenic host cells, in particular transgenic plant cells and plants.

In a further embodiment, the invention relates to a method for the caryopsis-specific gene expression in plants, wherein one or more of the nucleic acid molecules according to the invention is integrated stably into the genome of a plant cell, either directly or by means of one or more of the vectors, expression cassettes or host cells according to the invention, and a plant is regenerated from said plant cell.

In a further embodiment, the invention relates to a method for the caryopsis-specific gene suppression in plants, wherein one or more of the nucleic acid molecules according to the invention is integrated stably into the genome of a plant cell, either directly or by means of one or more of the vectors, expression cassettes or host cells according to the invention, and a plant is regenerated from said plant cell, preferably by means of cosuppression.

The plants according to the invention can be generated by methods known to the skilled worker, for example by transforming plant cells or tissue and regenerating intact plants from the transformed cells or the tissue.

In principle, a multiplicity of molecular-biological techniques is available for introducing DNA into a plant host cell. These techniques comprise the transformation of plant cells with T-DNA using *Agrobacterium tumefaciens* or *Agrobacterium rhizogenes* as transformation agent, the fusion of protoplasts, the injection, the electroporation of DNA, the introduction of the DNA by means of the biolistic approach etc.

When DNA is injected, electroporated and transformed by means of biolistic methods ('particle gun') into plant cells, no specific requirements as such are made to the plasmids used. Simple plasmids such as, for example, pUC derivatives can be used. However, if intact plants are to be regenerated from cells transformed thus, for example the presence of a selectable marker gene is necessary.

Depending on the method by which desired genes are introduced into the plant cell, further DNA sequences may be required. If, for example, the Ti or Ri plasmid are used for transforming the plant cell, at least the right border, but frequently the right and left border, of the Ti and Ri plasmid T-DNA must be linked to the genes to be introduced as flanking region.

If agrobacteria are used for the transformation, the DNA to be introduced must be cloned into specific plasmids, viz. either into an intermediary vector or into a binary vector. The intermediary vectors can be integrated into the Ti or Ri plasmid of the agrobacteria by homologous recombination owing to sequences which are homologous to sequences in the T-DNA. This Ti or Ri plasmid additionally contains the vir region, which is necessary for transferring the T-DNA. Intermediary vectors are not capable of replication in agrobacteria. The intermediary vector can be transferred to Agrobacterium tumefaciens by means of a helper plasmid (conjugation). Binary vectors are capable of replicating both in E.coli and in agrobacteria. They contain a selection marker gene and a linker or polylinker, which are framed by the right and left T-DNA border region. They can be transformed directly into the agrobacteria (Holsters et al. Mol. Gen. Genet. 163 (1978), 181–187). The agrobacterium acting as the host cell should contain a plasmid carrying a vir region. The vir region is necessary for transferring the T-DNA into the plant cell. Additional T-DNA may be present. The agrobacterium transformed thus is used to transform plant cells.

The use of T-DNA for transforming plant cells has been studied intensively and described sufficiently in EP 120 516; Hoekema, In: The Binary Plant Vector System Offsetdrukkerij Kanters B. V., Alblasserdam (1985), Chapter V; Fraley et al., Crit. Rev. Plant. Sci., 4, 1–46 and An et al. EMBO J. 4 (1985), 277–287.

To transfer the DNA into the plant cell, plant explants can expediently be cocultured together with Agrobacterium tumefaciens or Agrobacterium rhizogenes. Then, intact plants can be regenerated from the infected plant material (for example leaf sections, stem segments, roots, but also protoplasts, or plant cells grown in suspension culture) in a suitable medium which may contain antibiotics or biocides for selecting transformed cells. The plants thus obtained can then be examined for the presence of the DNA introduced. Other possibilities of introducing foreign DNA using the biolistic method or by protoplast transformation have been described (cf., for example, Willmitzer, L., 1993 Transgenic plants. In: Biotechnology, A Multi-Volume Comprehensive Treatise (H. J. Rehm, G. Reed, A. Pühler, P. Stadler, eds.), Vol. 2, 627–659, VCH Weinheim-New York-Basle-Cambridge).

Monocots have already been routinely transformed by means of the biolistic approach and by means of agrobacteria (Komari et al., (1998); Advances in cereal gene transfer; Current Opinion in Plant Biotechnology 1, p. 161 et seq.; Bilang et al. (1999), Transformation of Cereals, Genetic Engineering, 12, pp.113–148 Ed.: JK Setlow, Kluwer Academic/Plenum Publisher, New York). Other suitable methods are the electrically or chemically induced DNA uptake into protoplasts, the electroporation of partially permeabilized cells, the macroinjection of DNA into inflorescences, the microinjection of DNA into microspores and proembryos, the DNA uptake by germinating pollen, and the DNA uptake into embryos by soaking (review: Potrykus, Physiol. Plant (1990), 269–273).

The present invention furthermore also relates to the propagation material and harvested material of the plants according to the invention, which comprises plant cells according to the invention.

For the purposes of the present invention, the term "propagation material" extends to all those constituents of the plant which are suitable for generating progeny via the vegetative or generative route. Examples which are suitable for vegetative propagation are cuttings, callus cultures, rhizomes, root stocks or tubers. Other propagation material encompasses, for example, fruits, seeds, seedlings, protoplasts, cell cultures and the like. The propagation material is preferably tubers or seeds.

The present invention furthermore relates to the use of promoters according to the invention, or to the promoters identified by means of the method according to the invention, for the caryopsis-specific expression of transgenes in plant cells or plants.

Moreover, the present invention relates to the use of the promoters according to the invention, or of the promoters identified by means of the method according to the invention, for the caryopsis-specific cosuppression of genes or transgenes in plant cells or plants.

In this context, the term "transgene" is to be understood as meaning a DNA sequence which has been introduced artificially into a plant and which contains one or more of the nucleic acid molecules according to the invention.

These and other embodiments are disclosed to the skilled worker by the description and the examples of the present invention. Further literature on any of the abovementioned methods, means and applications required for the purposes of the present invention is known to the skilled worker from the prior art. The methods of choice which are suitable for this purpose are, inter alia, public databases (for example "Medline"), some of which are available via the Internet. Other databases and addresses are known to the skilled worker and can be found, if appropriate, on the Internet, for example using any known search engine. An overview over sources and informations on patents or patent applications in biotechnology can be found in Berks, TIBTECH 12 (1994), 352–364.

To describe the invention in greater detail, one of the promoters is represented by Seq ID No.1, consisting of 4 683 bases of the genomic sequence of the isolated SSII subclone p15/G such as deposited by DSM 14224.

Seq ID No.1 represents the DNA sequence of the genomic SSII subclone p15/G (insert size: 5057 base pairs). Nucleotides 1-4683 of Seq. ID No. 1 correspond to the 5'-flanking region of the gene, i.e. the SSII promoter. Subclone p15/G additionally contains 374 bases of the SSII structural gene (positions 4684 to 5057). An intron with a length of 91 bases is present at positions 4948 to 5038.

The isolated SSII cDNA clone (Walter (2000), PhD thesis University of Hamburg, School of Biology, WO 97/45545, or EMBL Database U66377) shows 83.7% homology with the genomic sequence stated in Seq ID No.1 in the 5'-untranslated region (positions 4512 to 4683). In the first exon (positions 4684–4947), there is 92.6% sequence identity with this cDNA sequence. The 5'-untranslated region and the first exon of the sequence stated under Seq ID No.1 (positions 4596–4947) is identical to the first 352 bp of a CDNA clone of an SSII (Theor. Appl. Genet., (1999), 98: 1208–1216), WSSIIA and the first 318 bp of the cDNA clone wss2a-2 (AJ269503), which has been published by Gao et al. (2000, loc.cit.).

The 5'-flanking DNA region of the isolated genomic clone (Seq ID. No.1, i.e. nucleotides 1–4683 of Seq. ID No. 1) has been compared with sequences which have already been published by means of database searches. The promoter region of a wheat SSII gene is a previously unknown sequence.

Moreover, the described DNA sequence, which flanks the start codon 5' (Seq ID No.1, nucleotides 1–4683) was searched in the PLACE database (http://www.dna.affrc.go.jp/htdocs/PLACE/; Web Signal Scan Program) for DNA motifs with sequence homology with known cis-regulatory elements. In the SSII promoter (i.e. nucleotides 1–4683 of Seq. ID No. 1, as deposited by DSM 14224), the following endosperm—or seed-specific cis-regulatory DNA elements were identified:

| Name (gene; organism) | Position (strand) | Signal sequence |
|---|---|---|
| -300 element (gliadins, glutenins; *T. aestivum*) | Position 941 (+) | TGHAAARK |
| | Position 3134 (+) | TGHAAARK |
| | Position 3406 (+) | TGHAAARK |
| | Position 580 (−) | TGHAAARK |
| -300 motif (zein; *Z. mais*) | Position 4467 (+) | TGTAAAG |
| Napin motif (2S albumin; *B. napus*) | Position 3311 (−) | TACACAT |
| (CA)<sub>n</sub> element (napA; *B. napus*) | Position 2285 (+) | CNAACAC |
| | Position 2714 (−) | CNAACAC |
| | Position 4420 (+) | CNAACAC |
| ACGT box (Glu-B1, *O. sativa*) | Position 2193 (+) | GTACGTG |
| | Position 2477 (+) | GTACGTG |
| Amylase box (α-amylase, *T. aestivum*) | Position 3534 (+) | TAACARA |
| CGACG element (amylase, *O. sativa*) | Position 195 (+) | CGACG |
| | Position 957 (+) | CGACG |
| | Position 1181 (+) | CGACG |
| | Position 2321 (+) | CGACG |
| | Position 1331 (−) | CGACG |
| | Position 2015 (−) | CGACG |
| | Position 2277 (−) | CGACG |
| | Position 4481 (−) | CGACG |
| E box (napA; *B. napus*) | Position 72 (+) | CACGTG (=G box) |
| | Position 866 (+) | CANNTG |
| | Position 1568 (+) | CANNTG |
| | Position 1594 (+) | CANNTG |
| | Position 2603 (+) | CANNTG |
| | Position 2980 (+) | CANNTG |
| | Position 3290 (+) | CANNTG |
| | Position 3447 (+) | CANNTG |
| | Position 3751 (+) | CANNTG |
| | Position 4032 (+) | CANNTG |
| | Position 4110 (+) | CANNTG |
| | Position 4174 (+) | CANNTG |
| | Position 4295 (+) | CACGTG (=G box) |
| RY repeat (Gy2; *V. faba*) | Position 2353 (+) | CATGCATG |
| RY repeat (Gy2; *G. max*) | Position 1590 (+) | CATGCAT |
| | Position 2353 (+) | CATGCAT |
| | Position 2532 (+) | CATGCAT |
| | Position 2354 (−) | CATGCAT |
| | Position 2471 (−) | CATGCAT |
| | Position 4146 (+) | CATGCAT |
| RY repeat (legumin; *G. max*) | Position 2088 (+) | CATGCAY |
| RY repeat (napA; *B. napus*) | Position 733 (−) | CATGCA |
| | Position 2355 (−) | CATGCA |
| | Position 2472 (−) | CATGCA |
| | Position 2601 (−) | CATGCA |
| SEF1 motif (7S globulin; *G. max*) | Position 2871 (+) | ATATTTAWW |
| | Position 3108 (+) | ATATTTAWW |
| | Position 2938 (−) | ATATTTAWW |
| SEF3 motif (7S globulin; *G. max*) | Position 403 (+) | AACCCA |
| | Position 1114 (−) | AACCCA |
| SEF4 motif (7S globulin; *G. max*) | Position 845 (+) | RTTTTTR |
| | Position 2787 +) | RTTTTTR |
| | Position 838 (−) | RTTTTTR |
| | Position 3047 (−) | RTTTTTR |
| | Position 3156 (−) | RTTTTTR |
| | Position 3274 (−) | RTTTTTR |
| | Position 3785 (−) | RTTTTTR |
| | Position 2876 (−) | RTTTTTR |
| | Position 3049 (−) | RTTTTTR |
| | Position 3099 (−) | RTTTTTR |
| | Position 3113 (−) | RTTTTTR |
| | Position 3198 (−) | RTTTTTR |
| | Position 3306 (−) | RTTTTTR |
| | Position 3571 (−) | RTTTTTR |
| | Position 3681 (−) | RTTTTTR |

Sequence homologies with elements which participate in gene expression which is regulated by sugar were found at the following positions:

| Name (gene; organism) | Position (Strand) | Signal sequence |
|---|---|---|
| ACGTA box (α-amylase; *O. sativa*) | Position 4450 (+) | TACGTA |
| CGACG element (AMY3; *O. sativa*) | Position 195 (+) | CGACG |
| | Position 957 (+) | CGACG |
| | Position 1181 (+) | CGACG |
| | Position 2321 (+) | CGACG |
| | Position 1331 (−) | CGACG |
| | Position 2015 (−) | CGACG |
| | Position 2277 (−) | CGACG |
| | Position 4481 (−) | CGACG |
| | Position 4484 (−) | CGACG |
| | Position 4688 (−) | GGACG |
| SURE1 (Sbe2.2; *A. thaliana*) | Position 3979 (+) | AACAGAAAA |

Sequence homologies with DNA elements which participate in hormonally-regulated gene expression by ABA or GA were found at the following positions:

| Name (gene; organism) | Position (strand) | Signal sequence |
|---|---|---|
| ABRE (rd22, *A. thaliana*) | Position 71 (+) | RYACGTGGY |
| ABRE motif A (Osem; *O.sativa*) | Position 2478 (+) | TACGTGTC |
| ABRE (Em, *T. aestivum*) | Position 1219 (+) | ACGTSSSC |
| | Position 1179 (−) | ACGTSSSC |
| | Position 2044 (−) | ACGTSSSC |
| EMBP1 (Em, *T. aestivum*) | Position 72 (+) | CACGTGGC |
| Pyrimidine box (EBP-1; *H. vulgare*) | Position 3459 (−) | TTTTTTCC |
| | Position 3479 (−) | TTTTTTCC |
| | Position 3608 (−) | TTTTTTCC |
| DPBF motif (Dc3; *D.carota*) | Position 4463 (−) | ACACNNG |
| LTRE (cor15a; *A.thaliana*) | Position 956 (+) | CCGAC |
| | Position 1772 (+) | CCGAC |
| | Position 2143 (+) | CCGAC |
| | Position 2222 (+) | CCGAC |
| | Position 2320 (+) | CCGAC |
| | Position 87 (−) | CCGAC |
| | Position 397 (−) | CCGAC |
| | Position 780 (−) | CCGAC |
| | Position 1214 (−) | CCGAC |
| | Position 4689 (−) | CCGAC |

Sequence homologies with elements which participate in a hormonally regulated gene expression by auxin or ethylene were found at the following positions:

| Name (gene; organism) | Position (strand) | Signal sequence |
|---|---|---|
| ASF-1 motif (35S; CaMV) | Position 192 (+) | TGACG |
| | Position 775 (+) | TGACG |
| | Position 819 (+) | TGACG |
| | Position 2150 (+) | TGACG |
| | Position 3694 (+) | TGACG |
| | Position 16 (−) | TGACG |
| | Position 1406 (−) | TGACG |
| | Position 1803 (−) | TGACG |
| | Position 4029 (−) | TGACG |
| | Position 4046 (−) | TGACG |
| Auxin response f. (ARF; *A.thaliana*) | Position 1539 (−) | TGTCTC |
| NtBBF1 motif (rolB; *A. rhizogenes*) | Position 3702 (+) | ACTTTA |
| Ethylene RE (E4; *L.esculentum*) | Position 3270 (+) | AWTTCAAA |

Sequence homologies with DNA elements which represent a light- or temperature-regulated gene expression were found at the following positions:

On Apr. 6, 2001, plasmid p15/G comprising Seq ID No.1 was deposited at the DSMZ under deposition number DSM 13398.

| Name (gene; organism) | Position (strand) | Signal sequence |
|---|---|---|
| I box (monocots and dicots) | Position 2883 (+) | GATAA |
|  | Position 463 (−) | GATAA |
|  | Position 2907 (−) | GATAA |
|  | Position 3065 (−) | GATAA |
|  | Position 3804 (−) | GATAA |
|  | Position 3920 (−) | GATAA |
|  | Position 3920 (−) | GATAA |
|  | Position 4087 (−) | GATAA |
| LTRE-1 (blt4.9; H. vulgare) | Position 179 (−) | CCGAAA |
| LTRE (lti; A. thaliana) | Position 2221 (+) | ACCGACA |
| LTRE (cor15a; A.thaliana) | Position 956 (+) | CCGAC |
|  | Position 1772 (+) | CCGAC |
|  | Position 2143 (+) | CCGAC |
|  | Position 2222 (+) | CCGAC |
|  | Position 2320 (+) | CCGAC |
|  | Position 4689 (+) | CCGAC |
|  | Position 87 (−) | CCGAC |
|  | Position 397 (−) | CCGAC |
|  | Position 780 (−) | CCGAC |
|  | Position 1214 (−) | CCGAC |

In addition to the sequence motifs described, homologies with DNA motifs for general transcription factors (for example GT1 consensus, G boxes, DOF boxes, GATA motifs, Myb and Myc boxes; for information, see PLACE database), and also T boxes and ARS elements (Gasser S. M. et al. (1989) Intnatl Rev Cyto 119:57–96) were found in the promoter.

The SSII promoter stated under Seq ID No.1 also exhibits sequence motifs which have not been described as yet. They include a motif of the sequence 5'-AAAAATGT-3', which occurs in total nine times in the region of from 3009 to 3329 of the sequence stated under Seq ID No.1 (positions: 3009, 3030, 3114, 3157, 3177, 3199, 3275, 3307, 3321). In contrast to this motif, the −300 element, also termed prolamin box, has the sequence motif 5'-TGTAAAG-3' and is located approximately 300 nucleotides from the transcription start in promoters of hordeins (barley), gliadins and LMW glutenins (wheat) and also α-zeins (maize) (Forde et al. (1985) Nucleic Acid Research 13: 7327–7339; Mena et al. (1998) Plant J. 16: 53–62).

Repeating short sequence motifs are located at position 4221 $(TCTA)_4$, at position 2304 $(GCCT)_3$ and position 2364 $(GCT)_3$. A direct repeat of sequence AAAAATGTAAT-CAAGCTTT (SEQ ID NO: 17) is located at positions 3199 and 3275. In the 5'-untranslated region directly before the translation start (position 4671 in Seq ID NO. 1) there is a GC-rich sequence CCCGGCCGCC (SEQ ID NO: 18), which is also present in the 5'-untranslated region of the maize zSSIIa cDNA clone before the translation start (Genbank Acc. No. AF019296; Harn et al. (1998) Plant Mol. Biol. 37: 639–649).

The genomic SSII subcdone p8/C, which is disclosed in German Patent Application DE10032379.0 and deposited by DSM 13397 constitutes a fragment of the sequence ID No. 1. In this respect, the content of DE10032379.0 is expressly incorporated into the present application by reference.

Deposition of Microorganisms

The nucleic acid molecule according to the invention as shown in Seq ID No. 1 was deposited at the Deutsche Sammlung für Mikroorganismen und Zelikulturen (DSMZ) in Brunswick, Germany, in compliance with the provisions of the Budapest Treaty by means of plasmid DNA:

Cloning Methods

The vectors pBluescript™ II, SK(+/−) and KS(+/−) phagemid vectors (Stratagene GmbH, Heidelberg, Germany) and Lambda Fix® II/Xhol cloning vector (Stratagene GmbH, Heidelberg, Germany) were used for cloning into E.coli bacterial strains.

Bacterial Strains

The E.coli strains DH5α (Life Technologies, Eggenstein, Germany) and Epicurian Coli SURE® (Stratagene GmbH, Heidelberg, Germany) were used for the Bluescript vectors. The Epicurian Coli strain XL1-Blue MRA (Stratagene) was used for the bacteriophage vectors.

As regards basic techniques in molecular biology or, for example, buffer compositions, reference is made to Sambrook et al. ((1989), Molecular Cloning; A Laboratory Manual, Second Edition; Cold Spring Harbour Laboratory Press).

The examples which follow illustrate the invention, but do not limit it in any way whatsoever.

USE EXAMPLES

1. Generation of the Genomic Wheat Library

To generate the genomic wheat library, total DNA was isolated from etiolated seedlings of *Triticum aestivum* L. cv. "Florida". To grow sterile etiolated seedlings, mature caryopses were incubated for 20 min in 1% NaOCl, 0.1% (v/v) Mucasol® (Merz & Co., Frankfurt, Germany) and subsequently washed 3× with $ddH_2O$. The caryopses were plated onto sterile MS medium (Murashige & Skoog (1962), Physiol. Plant. 15: 473–479), to which 0.3% (w/v) of GELRITE® (Carl Roth GmbH & Co., Karlsruhe, Germany) had been added for solidification. Growth took place in the dark at 26° C. Fourteen days after plating, the seedlings were cut off and frozen in liquid nitrogen.

The genomic DNA was digested partially with the restriction enzymes BamHI or Sau3AI (Life Technologies, Eggenstein, Germany). To this end, 3 aliquots of in each case 100 μg genomic DNA were restricted with 150 μl of the restriction buffers in question for 1 h at 37° C. in a total volume of 1.5 ml with 12.5 units, 6.25 units or 3.125 units of the restriction enzyme BamHI or 1.56 units, 0.78 units or 0.39 units of Sau3AI. Aliquots of the partially restricted DNA were then analyzed by gel electrophoresis for the degree of restriction. The restriction enzymes were removed from the reactions by extracting once with phenol/chloroform/isoamyl alcohol (25:24:1, v/v) and with chloroform/isoamyl alcohol (24:1, v/v). Finally, sucrose was added to each reaction to a final concentration of 10% (w/v).

Size fractionation of the partially restricted DNA was effected in continuous sucrose gradients (10–40% w/v) (Sambrook et al. (1989)). In each case a 15 ml sucrose gradient, the aliquots of the partially restricted DNAs were warmed for 10 min at 68° C. and then cooled to 20° C. The gradient was centrifuged for 24 h at 20° C. and 22000 rpm (Beckmann, Rotor SW 40). After centrifugation, the bottoms of the centrifuge tubes were pierced, and 500 µl aliquots were collected. 30 µl from the individual fractions were separated in a 0.5% agarose gel, and the size distribution of the DNA in the individual fractions was determined. Fractions containing genomic DNA of approx. 4.0 kb and above were combined. The sucrose from the samples was removed by dialysis against Tris/EDTA buffer (10 mM/1 mM). The samples were subsequently concentrated with 2-butanol and the DNA was precipitated from the samples at room temperature (RT) with 2 volumes of EtOH (99.8%)/2 M ammonium acetate (final concentration).

To fill up the 3' end of the partially restricted DNA, 20 µg of the DNA restricted with BamH I or Sau3A I were incubated in a final volume of 60 µl with 1 mM dATP, 1 mM dGTP (Roche, Mannheim), 6 µl 10× Pfu reaction buffer and 10 units native Pfu-DNA polymerase (DNA polymerase with "proof-reading" activity; Stratagene GmbH, Heidelberg, Germany). The reaction was carried out for 1 h 30 min at 72° C. The DNA was subsequently extracted with phenol/chloroform/isoamyl alcohol and with chloroform/isoamyl alcohol and subsequently precipitated with $\frac{1}{10}$ volume 3M NaAc and 2.5 parts by volume absolute EtOH.

1.1. Ligation into Lambda Fix® II/Xho I Partial Fill-In Vectors (Stratagene GmbH, Heidelberg, Germany)

The genomic DNA which have been restricted with BamHI or Sau3AI was ligated into the Lambda Fix® II/Xho I cloning vector following the manufacturer's instructions (Stratagene GmbH, Heidelberg, Germany). The ligation reaction contained: 1 µl of the Lambda Fix® II vector, 0.4 µg of genomic DNA restricted with BamHI or Sau3A I, 0.5 µl 10× ligation buffer, 2 Weiss units T4 DNA ligase (MBI Fermentas GmbH, St. Leon-Rot, Germany); Weiss et al. (1968) J. Biol. Chem., 243: 4543–4555) in a final volume of 5 µl.

1.2. In Vitro Packaging of the Ligation Products

To package the Lambda phages, the in vitro packaging kit "Gigapack® II Gold" by Stratagene (Stratagene GmbH, Heidelberg, Germany) was used, following the manufacturer's instructions.

1 µl of each of the ligation reactions was added to the packaging reactions; the rest was as described in the manufacturer's instructions.

1.3. Growing Bacteria for Phage Amplification

The E.coli bacterial strain XL1-Blue MRA (P2) was used for phage amplification. The bacteria were grown in LB medium supplemented with 10 mM $MgSO_4$, 0.2% (w/v) maltose, to an $OD_{600}$=0.5 at 37° C., 180 rpm. The bacteria was subsequently pelleted for 10 min at 4° C. at 2000 rpm and the supernatant was discarded. The bacterial pellet was resuspended in 10 mM $MgSO_4$ and the bacterial density was adjusted to $OD_{600}$=0.5.

For phage amplification, from the packaging reactions 1 µl from the original reactions or 1:10 dilution of the original reactions were mixed with 200 µl of bacterial suspension ($OD_{600}$=0.5) and incubated for 15 min at 37° C. The individual reactions were subsequently mixed with 3 ml of TOP agarose (48° C.) and plated onto solid NZY medium following the manufacturer's instructions (see above Lambda Fix® II/Xho I Partial Fill-In vectors, Stratagene). The plates were incubated for approximately 16 h at 33° C.

The phage titer of the genomic Sau3AI or BamHI libraries were determined by counting the phage plaques. For the primary Sau3aI or BamHI libraries, phage titers of $2.2 \times 10^7$ pfu/ml and $1.4 \times 10^7$ pfu/ml, respectively, were determined. To determine the average insert sizes, 10 individual phage clones from each library were amplified, the phage DNA was isolated (Sambrook et al. 1989), and the insert sizes were determined following restriction digestion and separation by gel electrophoresis. The average insert size is approx. 15.0 kb for the BamHI library and 15.6 kb for the Sau3AI library.

1.4. Amplification of the Genomic Libraries

To generate representative amplified genomic libraries, approx. 4.5 million pfu from each library were plated. Amplification was performed following the manufacturer's instructions (Stratagene). The phage titers of the amplified libraries were $6.3 \times 10^9$ pfu/ml (BamHI library) and $2.0 \times 10^9$ pfu/ml (Sau3AI library).

2. Screening of the Genomic Libraries

Phage clones whose genomic inserts carry sequences of the ssII genes were identified and isolated via colony-plaque hybridization. To screen the genomic libraries, approx. 500,000 phages from each library were plated out. The phages were plated out and the plates were lifted following standard protocols (Sambrook et al., 1989; Stratagene Lambda Fix II® manual).

A 709 bp DNA fragment of a cDNA clone of an SSII (WO 97/45545 A1, EMBL database U66377, Walter (2000), PhD thesis University of Hamburg, School of Biology, positions 1264–1973) was employed as gene-specific probe.

The SSII probe was amplified from an isolated SSII cDNA clone via a PCR reaction using sequence-specific primers. Labeling of the 709 bp amplification product (positions 1264–1972 of the SSII cDNA) was carried out during the PCR reaction by incorporating DIG-dUTPs (Roche Diagnostics GmbH, Mannheim).

The PCR reaction was composed as follows:

10 µl PCR buffer (10×, Mg-free; Life Technologies)

3 µl $MgCl_2$ (50 mM; Life Technologies)

7 µl DIG dUTPs (1 nmol/µl; Roche Diagnostics GmbH, Mannheim)

8 µl each dATP, dCTP and dGTP (2.5 mM of each)

5 µl dTTP (2.5 mM)

5 µl primer LW2 (10 pmol/µl)

5 µl primer LW9 (10 pmol/µl)

10 ng template (cDNA clone of SSII)

0.5 µl Taq polymerase (5 U/µl; Life Technologies)

$ddH_2O$ to 100 µl

The PCR conditions were as follows:

I. 96° C., 5 min
II. 96° C., 1 min
III. 58° C., 1 min
IV. 72° C., 1 min (IV.→II. 29 loops)
V. 72° C., 5 min The sequences of the SSII-specific primers for amplification of the PCR probe were:

LW2: 5'-CTGCTGGACAGGATATGGAA-3' (SEQ ID No. 11)

LW9: 5'-TCGCGCTGCAGGGCCTCCTT-3' (SEQ ID No. 12)

The filters were prehybridized in 5× SSC, 3% blocking reagent (Boehringer Mannheim), 0.2% sodium dodecyl sulfate (SDS), 0.1% N-laurylsarcosin and 30 µg/ml herring sperm DNA in a water bath at 65° C. Hybridization with the DIG-labeled DNA probes (6 ng/ml hybridization solution) was carried out overnight at 65° C. in the above-described standard hybridization buffer. All further steps of the CSPD® chemoluminescence reaction were performed following the manufacturer's instructions (Roche Diagnostics GmbH, Mannheim, Germany).

Positive plaques were picked out and singled out over two individual amplification and plaque filter hybridization passages. The DNA of the isolated positive phages were purified with the Qiagen® Lambda Kit (Qiagen GmbH, Hilden, Germany), cleaved with various restriction enzymes and, following agarose gel electrophoresis, analyzed in Southern hybridizations with the probes which have been described above.

3. Subcloning of the λ-phage Clones into Bacterial Vectors (pBluescript™ II)

Positive phage clones of the genomic library were identified with the abovementioned gene-specific probe (709 bp). The genomic inserts of the positive phage clones were cleaved with various restriction enzymes or enzyme combinations to give shorter fragments. The resulting subfragments were cloned into bacterial vectors (pBluescript™ II SK(+/−) and KS(+/−) phagemid vectors; Stratagene GmbH, Heidelberg, Germany).

SSII specific subclones with 5'-upstream regulatory elements were isolated via Southern hybridizations. To this end, a further digoxigenin-labeled probe was generated which is located in the outermost 5' region of the SSII cDNA sequence. The probe extends from the 5'-untranslated region of the cDNA clone of the SSII into the first exon (positions 1–218 of the SSII-cDNA of WO 97/45545 A1). The fragment was excised from the SSII cDNA (in pBluescript™ SK II) via restriction digest with SmaI and isolated after separation by agarose gel electrophoresis. Labeling of the SmaI fragment was carried out by random priming with the DIG DNA Labeling Kit, following the manufacturer's instructions (Roche Diagnostics GmbH, Mannheim, Germany).

After digest of phage clone 15 with the enzyme XbaI, a subclone with 4682 base pairs which 5'-flanks its structural gene was identified (p15/G; Seq ID No.1, as deposited on Apr. 6, 2001, at the DSZM in Brunswick under the number DSM 14224). SacI digest resulted in a subclone with 2462 base pairs and 5'-flanking the structural gene, which subclone corresponds to clone p8/C deposited at the DSZM in Brunswick, Germany, under the number DSM 13397 (corresponding to Seq ID No.2 of German Patent Application DE 10032379.0). Subclone 15/G was sequenced fully and used for cloning promoter test vectors.

4. Sequence Analyses

SeqLab GmbH (Göttingen, Germany) was commissioned to sequence the genomic clones of the SSII.

5. Cloning Promoter Test Vectors

The functionality of the 5'-flanking DNA region cited in Seq ID No.1 were verified in transient and stable expression analyses. The reporter gene used was the β-glucuronidase (GUS) gene (Jefferson (1987) Plant Molecular Biology Reporter 5 (4): 387–405). Promoter test vectors were cloned in which the coding region of the gus gene (uidA) is under the control of the 5'-flanking DNA region stated in Seq ID No.1 (nucleotides 1–4683). Cloning was performed as a transcriptional fusion. First, the uidA gene together with the nos terminator was excized from vector pCal-GUS (uidA gene under the control of the CaMV 35S promoter; Chris Warren, Stanford University, unpublished) via a partial digest and cloned behind the multiple cloning site of pBluescript (Stratagene). The promoter-free vector thus generated (uidA-nos) was used for the further cloning steps.

The 5'-untranslated leader sequence of an mRNA may also affect the tissue specific expression of a gene (Rouster et al. (1998) Plant J. 15 (3): 435–40). The cloned promoter test vectors therefore contain this region of the SSII gene. In the cloning strategy chosen, the β-glucuronidase translation start codon is at the position of the SSII gene start codons.

5.1. Cloning the SSII Promoter Test Vectors

Cloning of an SSII promoter test vector by transcriptionally fusing the SSII promoter to the reporter gene uidA was carried out by the "splicing by overlap extension" method (Horton (1997) Methods in Molecular Biology Vol.67: PCR Cloning Protocols (14): 141149, White Humana Press Inc.).

To this end, a 2499 bp fragment of the genomic SSII subclone p15/G was first cloned into the promoterless plasmid uidA-nos via restriction digest with SacI (position 2241) and SmaI (position 4740).

The generation of intermediate products for the "splicing by overlap extension" method was carried out using the following primer pairs (in analogy with DE 10032379.0):

a) Amplification reaction with genomic SSII subclone as template:

SOE-A   5'-TCACGTGGATTCTGCAACCTC-3'           (SEQ ID No. 13)
SOE-B   5'-CAGGACGGACCATGGCGGCGGCCGGGAT-3'    (SEQ ID No. 14)

b) Amplification with plasmid pCaIGUS as template:

SOE-C   5'-CGCCGCCATGGTCCGTCCTGTAGAAACCC-3'   (SEQ ID No. 15)
SOE-D   5'-GTGATGTCAGCGTTGAACTGC-3'           (SEQ ID No. 16)

The reactions were carried out by the method of Horton (Methods in Molecular Biology (1997) Vol. 67: PCR Cloning Protocols (14): 141149, White Humana Press Inc.), the PCR conditions were:

I. 94° C., 90 sec
II. 94° C., 1 min
III. 64° C., 1 min
IV. 72° C., 1 min (IV.→II. 20 loops)
V. 72° C., 3 min Amplification of the PCR product for cloning was carried out with the primer sequences SOE-A and SOE-D. The templates used were the intermediates generated. The reaction was set up by the method of Horton (Methods in Molecular Biology (1997) Vol. 67: PCR Cloning Protocols (14): 141149, White Humana Press Inc.), the PCR reaction conditions were:

I. 96° C., 2 min
II. 94° C., 1 min
III. 68° C., 2 min
IV. 72° C., 2 min (IV.→II. 25 loops)
V. 72° C., 10 min Cloning of the resulting PCR product between the SSII promoter and the uidA gene was carried out following restriction digest with the enzymes Not I (cleavage site in the SSII promoter, position 4402) and BalI (cleavage site in the uidA gene). The SSII promoter test construct thus obtained bears 2443 bp 5'-flanking of the SSII gene (−2.45 SSII/GUS). Ligation of the missing distal 2240 bp of the SSII promoter (SacI fragment of 15/G) into the SacI cleavage site of construct −2.45 SSII/GUS gave rise to the construct −4.68/GUS, which bears all of the region described under SEQ. ID No.1 (nucleotides 1–4683) 5'-flanking of the SSII gene.

The 2443 bp region of construct −2.45 SSII/GUS was subsequently truncated further by deletions. The deletions were carried out by restrictions with different restriction enzymes, removing regions with described DNA elements in the promoter. In total, the following test constructs of the SSII promoter were cloned:

−4.68 SSII/GUS
−2.45.SSII/GUS (SacI restriction at position 2241, Seq ID No.1);
−2.05 SSII/GUS (KpnI restriction at position 2637, Seq ID No.1);
−1.11 SSII/GUS (SpeI restriction at position 3567, Seq ID No.1);
−0.61 SSII/GUS (HindIII restriction at position 4071, Seq ID No.1);
−0.53 SSII/GUS (SphI restriction at position 4151, Seq ID No.1) and
−0.28 SSII/GUS (NotI restriction at position 4403, Seq ID No.1);

6. Transient Expression Analyses of the Promoter Test Vectors

The functionality of the promoter constructs isolated was verified in transient expression analyses. The tests were carried out with the SSII promoter test vectors and their deletion constructs of Example 5.

The transient expression analyses were carried out following the biolistic transformation of various tissues (caryopses, embryos, leaves, roots) of wheat. Embryos, leaves and roots were transformed as described by Becker et al. (Plant J. (1994) 5 (2): 229–307), while the biolistic transformation of the endosperm of caryopses was carried out following a modified method of Mena et al. (Plant J. (1998) 16(1), 53–62). The reporter gene activity was detected by histochemically detecting GUS activity (Jefferson (1987) Plant Molecular Biology Reporter Vol.5 (4): 387–405). The experiments on 10–30 day old (dap) wheat caryopses which had been cut horizontally and vertically demonstrated that the SSII promoter leads to expression of the reporter gene in the starch endosperm of the caryopsis. No GUS activity was detected in other tissues (pericarp, leaves, roots).

The following deletion constructs of the GBSS I promoter proved to be functional in transient expression analyses:

−4.68 SSII/GUS
−2.45 SSII/GUS (SacI restriction at position 2241, Seq ID No.1)
−2.05 SSII/GUS (KpnI restriction at position 2637, Seq ID No.1);
−1.11 SSII/GUS (SpeI restriction at position 3567, Seq ID No.1)
−0.61 SSII/GUS (HindIII restriction at position 4071, Seq ID No.1)

In contrast, construct −0.28 SSII/GUS (NotI restriction at position 4403; Seq ID No.1) no longer shows GUS reporter gene activity.

The results of transient expression analyses of a promoter/reporter gene construct do not always correspond to the expression pattern following stable integration into the plant genome. In addition, the results of transient expression analyses following particle bombardment can vary greatly owing to the variability of the cells which have been hit. Further analyses on the tissue specificity of the isolated promoters were therefore carried out on stably transformed plants.

7. Stable Transformation of Wheat with the Promoter Test Vectors

To generate stably transformed wheat plants, the promoter test vector −4.68 SSII/GUS, which has been described in Example 5, and the deletion constructs −2.45 SSII/GUS and −0.61 SSII/GUS, which were also described there, were used.

The transgenic plants were generated following the method of Becker et al. (Plant J. (1994) 5 (2): 229–307). The selection marker used was plasmid p35S-PAT (comprising the pat gene, Aventis CropScience GmbH, Frankfurt), which carries phosphinothricin resistance.

8. Analysis of the GUS Reporter Gene Expression in Stably Transformed Wheat Plants The functional analysis of the SSII promoter fragments was carried out following regeneration of the transgenic plants and the verification of stable and complete integration of the test constructs into the wheat genome via Southern analyses.

The reporter gene activity in the transgenic plants regenerated was studied via a histochemical GUS detection. Various tissues of the transgenic plants (leaves, roots, endosperm, embryo, pollen) were analyzed. A reporter gene activity was detected exclusively in the caryopses of the transgenic plants. Here, it emerged that the GUS activity was located in the central starch endosperm. In contrast, no GUS activity was detected in the embryo, the aleuron and in the region surrounding the embryo; nor was any reporter gene activity detected in the assimilating tissue of the leaves, and in the roots and in the pollen.

In the functional analyses carried out, the 4683bp 5' flanking the ssII gene which are described under Seq ID No.1 show tissue-specific expression of the transgene exclusively in the starch endosperm of the caryopses. The deleted fragments of the promoter isolated (positions 2241 to 4683, and 4071 to 4683 respectively) also continue to mediate tissue-specific expression of the transgene.

What is claimed is:

1. An isolated nucleic acid molecule with the function of a caryopsis-specific promoter, which nucleic acid molecule:
   a) has the nucleotide sequence of nucleotides 1–4683 of SEQ ID NO: 1; or
   b) comprises a functional portion of the nucleotide sequence stated under a), wherein the functional portion comprises bases 2241–4683 or 4071–4683 of SEQ ID NO: 1.
   c) with the nucleotide sequence stated under a under hybridization conditions comprising a hybridization temperature of 65–68° C., a wash temperature of 65–68° C., and a wash buffer salt concentration of 0.2×SSC; or
   d) has about 90–95% identity with the sequence stated under a).

2. The isolated nucleic acid molecule as claimed in claim 1, which is a promoter active in monocots.

3. An expression cassette comprising a nucleic acid molecule as claimed in claim 1.

4. A vector comprising a nucleic acid molecule as claimed in claim 1 or an expression cassette as claimed in claim 3.

5. The vector as claimed in claim 4, which is suitable for transforming plant cells.

6. A plant, fungal or bacterial host cell which is genetically modified with the nucleic acid molecule as claimed in claim 1, with the expression cassette as claimed in claim 3, with a vector comprising the nucleic acid molecule as claimed in claim 1, or with a vector comprising the expression cassette as claimed in claim 3.

7. The host cell as claimed in claim 6, which is a plant cell.

8. A plant comprising plant cells as claimed in claim 7.

9. Propagation material or harvested material from plants as claimed in claim 8, wherein the material comprises said nucleic acid molecule.

10. A method of generating transgenic plant cells wherein plant cells are transformed with the nucleic acid molecule as claimed in claim 1, with the expression cassette as claimed in claim 3, with a vector comprising the nucleic acid molecule as claimed in claim 1, or with a vector comprising the expression cassette as claimed in claim 3, and wherein the transformed plant cells are cultivated in a growth medium.

11. A method of generating transgenic plants wherein plant cells, plant tissue, plant parts or protoplasts are transformed with the nucleic acid molecule as claimed in claim 1, with the expression cassette as claimed in claim 3, with a vector comprising the nucleic acid molecule as claimed in claim 1, or with a vector comprising the expression cassette as claimed in claim 3, and wherein the transformed plant cells, plant tissues, plant parts or protoplasts are grown in a growth medium, and regenerated into intact plants.

12. A method for the caryopsis-specific gene expression in plants, wherein a nucleic acid molecule as claimed in claim 1 is stably integrated into to the genome of a plant cell, and a transformed plant is regenerated from said plant cell.

* * * * *

SEQUENCE LISTING

<160> NUMBER OF SEQ ID NOS: 18

<210> SEQ ID NO 1
<211> LENGTH: 5058
<212> TYPE: DNA
<213> ORGANISM: Triticum aestivum

<400> SEQUENCE: 1

| | | | | | |
|---|---|---|---|---|---|
| tctagagagg | tcacccgtca | gtctatccta | agcgtgaagg | ggtcatgagc | caatcactct | 60 |
| aagcactcct | gcacgtggcg | cgactggtcg | gggaccaagc | ccacctctat | atacacagca | 120 |
| ggcatgccgc | tcaccccaac | aatcagcccg | cagtctgtac | tgtgacatca | ggcagagctt | 180 |
| tcggaggaa | ctgacgacgc | tgaggggccc | atacaccata | atcccacggg | gtgattagtg | 240 |
| tgtatatgcc | agtgacagtc | tcagatcaaa | tactcaaatc | ttgttgagcg | tgttattaag | 300 |
| aaataacctt | ggacatcgac | cagggcccag | gcccacttct | ctcctaggtg | gtctctacct | 360 |
| gccttgtcgt | tccgccacgt | tgaatcactc | gaggctgtcg | ggaacccagg | cctatcacta | 420 |
| cctagatggt | accatctatt | ccttcagccc | ttagttcgaa | cattatcata | agtattacgt | 480 |
| tattatatag | tatatctgtg | atcattggcc | aaagagacca | cggctcaata | atgtagcaat | 540 |
| gcaaacggtg | agactctagc | agacaactaa | catttattta | ctttgcagcg | aagcacgggt | 600 |
| gattcaagat | agttctaatt | tttttaaaga | cggttctaat | tcttttttt | acggcaacac | 660 |
| ggttctaatt | ctaccgttgc | aacgcacaag | gagatgtgct | ggtctctaac | aatgtatgta | 720 |
| ggagtttttt | gttgcatgga | tcggacggtt | gaagatcgta | atataagtca | cctttgacgg | 780 |
| tcgggaaaat | ggcggttatt | tctgtgtttt | cagacggctg | acgcctggca | atcaccccaa | 840 |
| aaatatttt | gtatgcgagg | aggatcacct | gccgccggct | gacatccgcc | acatcagtag | 900 |
| gttaggccaa | ctcctccgct | tgccaccgaa | ttaagctcgc | tgaaaagttc | ccctcccgac | 960 |
| gcttcgcagg | taggtaggtg | catccatccc | caactccccg | gccgtgccgc | acaccccat | 1020 |
| ctatatatgc | aaatccagtc | cattcctgat | caaccaggac | ttgattagta | gagcaagagg | 1080 |
| cctgaacaag | cacgcgctcg | cagatcatcg | acatggggttg | tgagaggacg | ccgctggccg | 1140 |
| ttgctctggc | actggccctg | ctcctgggcc | tcgcccacgg | cgacgtggtg | cagttcatct | 1200 |
| tcggcgactc | gctgtcggac | gtgggcaaca | acaactacct | gaccaagagc | ctcgcgcgcg | 1260 |
| cggcgctgcc | gtggtacggc | atcgacttcg | gcagcggcat | gcccaacggc | aggttctgca | 1320 |
| acggccgcac | cgtcgcggac | atcatcggcg | acaagatggg | cctcccgcgc | ccgcccgcgt | 1380 |
| tcctggaccc | gtccgtggac | gagaccgtca | tcgccaagag | cggcctcaac | tacgcgtccg | 1440 |
| gcggcggcgg | catcctcaac | gagacctcgt | ccctcttcgt | aagacaccca | tccatcactt | 1500 |
| caccaacttc | tcgtagctag | acagcatggt | agtatcatga | gacatgaacg | ctccggttcg | 1560 |
| atcatcgcat | ctgactgaga | cccatggcgc | atgcatttgc | agatccagag | gttctcgctg | 1620 |
| tacaagcaga | tcgagctgtt | ccaggggacg | caggcgttca | tgcgggagaa | gatcgggcgg | 1680 |
| gcggcggcg | acaagctgtt | cggcgaggcc | tactacgtgg | tggccatggg | cgccaacgac | 1740 |
| ttcatcaaca | actacctgct | ccccgtctac | tccgactcgt | ggacctacaa | cggcgacacc | 1800 |
| ttcgtcaagt | acatggtcac | cacccctggag | gcccagctcc | ggctcctgca | cgggctgggc | 1860 |
| gcgcgccggg | tcaccttctt | cgggctgggg | cccatgggct | gcatcccgct | gcagcggctc | 1920 |
| ctgcagaggt | cctccacggc | gtgccaggag | tccaccaaca | agctcgccct | cagcttcaac | 1980 |
| aagcaggccg | gcgcggtgat | cagggagctg | gcggcgtcgc | tgcccaacgc | cacgttccag | 2040 |

```
ttcggggacg tctacgacta cttccaggac atcatcgacc gcccctacat gcacggcttc    2100
aacaactccc acgcgccctg ctgcacgctc ggcaaggtgc ggccgaccct gacgtgcacc    2160
ccgctctcca cgctctgcaa ggaccgcagc aagtacgtgt tctgggacga gtaccacccc    2220
accgacaggg ccaacgagct catcgcgctc gagacgctca agcggctcaa catcaccgtc    2280
gttgccaaca ccacctccag ctagcctgcc tgcctgccac cgacgccgcc caccaaaatg    2340
cgtacgcttc gacatgcatg ggcgctgctg ctgtgtgttg tcttaattat actgcgggtg    2400
cttcgattgt aaccaaagta ggatgatcga aaattctagg atgatgtcca agaaatggga    2460
tggagaatag atgcatgtac gtgtcctgga tatgaaattt ttttgagtat gagagaacag    2520
cataccagga tcatgcatct atcttaaatc tcaagaggcc actattaaga cgttgatgtt    2580
taagacggtg atgttctatt tgcatgtgaa atttcaagtt caaagacggt accatttatg    2640
agctatggaa tcagccatga atagtgatgt ttactgttga cactattcat tgctgctttt    2700
gtcttttggt aatgtgtttg aacttggaaa tttcacatac taatagaaca tcacactctt    2760
aagacgtaat atttctttga gattttatttt ttgaaacttc gcctgaaggg tgctgatgtg    2820
cccgctattc atctaggaga ctaggaaaat atatgcaaaa aaattcatac atatttaaaa    2880
atgataaata tgtatagaga aaatgtttat caactataga aaaatatatg caaaaaatat    2940
aaatatgtat gaattttttt agcaagtatt taaatctagc atttgaaaga aaaataaaca    3000
agtattagaa aaatgttaaa cgtgtataga aaaatgttac catgtaatta aaaattgtat    3060
aaaattatca tgtattttta aaaaaataac caagcattta aaaacaaata tttaaaaatg    3120
ttaataaagg atttgaaaaa ttctaaacgt gtatacaaaa atgttgacca tgtattaaaa    3180
aatgttaatc ttgtatttaa aaatgtaatc aagcatttag aaaaacagtt aaattgtata    3240
gaaatgtacc cagaaaatct tgatattata tttcaaaaat gtaatcaagc atttgaaaaa    3300
tattttaaaa atgtgtatag aaaaaatgtt aaccatgtat ttaaaaaatt ttaaacttgt    3360
atttgaaaca tgttaatcat gtattagata tataccaaat atgtatgtaa aataacaatg    3420
aaaatccaag ggaaacgaaa gaaaaacaaa tgaaaacggg aaaaaaacaa aaaatgaagg    3480
aaaaaaaaga aaaacattg aaaaccaaga aagaaacaaa gagaaccgga gaataacaaa    3540 caaagggaa agaaaaggtg aaaaaactag taaaaacaag aaacaaagaa aaaggatga    3600 caaacaagga aaaaaattaa aaatccggaa aggcaacggt aagacgactc ttttccttca    3660
agttggtagc gccctaccag ggtaacacga acttgacgat gactttatgg ctaggagagc    3720
tacgctggaa cgaggagatc cggaccaaac catgtgcgct acaaaagtgt attattattt    3780
tttgcaaaaa tgatccgaat ctattatcaa aattcagcga aatacaaaac atctcgaaca    3840
taatgaacaa tacattgaga ttccaggacc ccaaacaacc actactgccg cgaagaaaaa    3900
aggattggga ggacagaaat tatcctaacc acgttcgtcc tcggttgttg gtctcatcgc    3960
gcgctaaaca acctggacaa cagaaaaggc aaagcagtgt cctccgctcc gcagcaaaga    4020
agacaaatcg tcacttgtca gaggccgtca cccaagcaag caaactgcaa agcttgttcg    4080
tttggtttat cccgtagtac gcgccaacgc atgtgccgca ccgcgtttgc ggtggagagc    4140
gcaggcatgc atcaaccaac aaacgaaaca gtgcagttgc ttacagtgct ccatccctcc    4200
aaaaaaaaaa gttgcagtgc tctatctatc tatctacaca atcaacgcgg gcctcctgct    4260
ccttcgccgc aagccccgtt ccgtcctcag tcttcacgtg gattctgcaa cctccttcca    4320
gcagcttgtc accacggacg cttcctcgtg cgctgctcgc gtggcaccgg ccccgctttc    4380
```

```
cagcgtgctc cgcgcgggcc gcggccgcaa atcgcagacc caacacgcca cccgccaggg    4440
ggccgttcgt acgtacccgc ccctcgtgta aagccgccgc cgtcgtcgcc gtcccccgct    4500
cgcggccatt tccccggcct gaccccgtgc gtttacccca cagagcacac tccagtccag    4560
tccagcccac tgccgccgcg ctactcccca ctcccgctgc caccacctcc gcctgcgccg    4620
cgctctgggc ggaggaccaa cccgcgcatc gtaccatcgc ccgccccgat cccggccgcc    4680
gccatgtcgt cggcggtcgc gtccgccgcg tccttcctcg cgctcgcctc cgcctccccc    4740
gggagatcac gcaggcgggc gagggtgagc gcgccgccac cccacgccgg ggccggcagg    4800
ctgcactggc cgccgtggcc gccgcagcgc acggctcgcg acgaggtgt ggccgcgcgc    4860 gccgccggga agaaggacgc gagggtcgac gacgacgccg cgtccgcgag gcagccccgc    4920
gcacgccgcg gtgcgccgc caccaaggta gttggttcgt tatgacttgc tgtatggcgc    4980
gtgcgcctcg agatcagctc acgaattgtt tctacaaaac gcacgcgctc gtgtgcaggt    5040
cgcggagcgg agggatcc                                                 5058

<210> SEQ ID NO 2
<211> LENGTH: 844
<212> TYPE: DNA
<213> ORGANISM: Triticum aestivum

<400> SEQUENCE: 2
tctagagagg tcacccgtca gtctatccta agcgtgaagg ggtcatgagc caatcactct    60
aagcactcct gcacgtggcg cgactggtcg gggaccaagc ccacctctat atacacagca    120
ggcatgccgc tcaccccaac aatcagcccg cagtctgtac tgtgacatca ggcagagctt    180
tcgggaggaa ctgacgacgc tgaggggccc atacaccata atcccacggg gtgattagtg    240
tgtatatgcc agtgacagtc tcagatcaaa tactcaaatc ttgttgagcg tgttattaag    300
aaataacctt ggacatcgac cagggcccag gcccacttct ctcctaggtg gtctctacct    360
gccttgtcgt tccgccacgt tgaatcactc gaggctgtcg ggaacccagg cctatcacta    420
cctagatggt accatctatt ccttcagccc ttagttcgaa cattatcata agtattacgt    480
tattatatag tatatctgtg atcattggcc aaagagacca cggctcaata atgtagcaat    540
gcaaacggtg agactctagc agacaactaa catttattta ctttgcagcg aagcacgggt    600
gattcaagat agttctaatt tttttaaaga cggttctaat tcttttttttt acggcaacac    660 ggttctaatt ctaccgttgc aacgcacaag gagatgtgct ggtctctaac aatgtatgta    720 ggagttttt gttgcatgga tcggacggtt gaagatcgta atataagtca cctttgacgg    780
tcgggaaaat ggcggttatt tctgtgtttt cagacggctg acgcctggca atcaccccaa    840
aaat                                                                844

<210> SEQ ID NO 3
<211> LENGTH: 880
<212> TYPE: DNA
<213> ORGANISM: Triticum aestivum

<400> SEQUENCE: 3
atttttgtat gcgaggagga tcacctgccg ccggctgaca tccgccacat cagtaggtta    60
ggccaactcc tccgcttgcc accgaattaa gctcgctgaa aagttcccct cccgacgctt    120
cgcaggtagg taggtgcatc catccccaac tccccggccg tgccgcacac ccccatctat    180
atatgcaaat ccagtccatt cctgatcaac caggacttga ttagtagagc aagaggcctg    240
aacaagcacg cgctcgcaga tcatcgacat gggttgtgag aggacgccgc tggccgttgc    300
```

```
tctggcactg gccctgctcc tgggcctcgc ccacggcgac gtggtgcagt tcatcttcgg      360
cgactcgctg tcggacgtgg gcaacaacaa ctacctgacc aagagcctcg cgcgcgcggc      420
gctgccgtgg tacggcatcg acttcggcag cggcatgccc aacggcaggt tctgcaacgg      480
ccgcaccgtc gcggacatca tcggcgacaa gatgggcctc ccgcgcccgc ccgcgttcct      540
ggacccgtcc gtggacgaga ccgtcatcgc caagagcggc ctcaactacg cgtccggcgg      600
cggcggcatc ctcaacgaga cctcgtccct cttcgtaaga cacccatcca tcacttcacc      660
aacttctcgt agctagacag catggtagta tcatgacaca tgaacgctcc ggttcgatca      720
tcgcatctga ctgagaccca tggcgcatgc atttgcagat ccagaggttc tcgctgtaca      780
agcagatcga gctgttccag gggacgcagg cgttcatgcg ggagaagatc gggcgggcgg      840
cggcggacaa gctgttcggc gaggcctact acgtggtggc                            880

<210> SEQ ID NO 4
<211> LENGTH: 516
<212> TYPE: DNA
<213> ORGANISM: Triticum aestivum

<400> SEQUENCE: 4
catgggcgcc aacgacttca tcaacaacta cctgctcccc gtctactccg actcgtggac       60
ctacaacggc gacaccttcg tcaagtacat ggtcaccacc ctggaggccc agctccggct      120
cctgcacggg ctgggcgcgc gccgggtcac cttcttcggg ctgggcccca tgggctgcat      180
cccgctgcag cggctcctgc agaggtcctc cacggcgtgc caggagtcca ccaacaagct      240
cgccctcagc ttcaacaagc aggccggcgc ggtgatcagg gagctggcgg cgtcgctgcc      300
caacgccacg ttccagttcg gggacgtcta cgactacttc caggacatca tcgaccgccc      360
ctacatgcac ggcttcaaca actcccacgc gccctgctgc acgctcggca aggtgcggcc      420
gaccctgacg tgcaccccgc tctccacgct ctgcaaggac cgcagcaagt acgtgttctg      480
ggacgagtac caccccaccg acagggccaa cgagct                                516

<210> SEQ ID NO 5
<211> LENGTH: 502
<212> TYPE: DNA
<213> ORGANISM: Triticum aestivum

<400> SEQUENCE: 5
catcgcgctc gagacgctca agcggctcaa catcaccgtc gttgccaaca ccacctccag       60
ctagcctgcc tgcctgccac cgacgccgcc caccaaaatg cgtacgcttc gacatgcatg      120
ggcgctgctg ctgtgtgttg tcttaattat actgcgggtg cttcgattgt aaccaaagta      180
ggatgatcga aaattctagg atgatgtcca agaaatggga tggagaatag atgcatgtac      240
gtgtcctgga tatgaaattt ttttgagtat gagagaacag cataccagga tcatgcatct      300
atcttaaatc tcaagaggcc actattaaga cgttgatgtt taagacggtg atgttctatt      360
tgcatgtgaa atttcaagtt caaagacggt accatttatg agctatggaa tcagccatga      420
atagtgatgt ttactgttga cactattcat tgctgctttt gtcttttggt aatgtgtttg      480
aacttggaaa tttcacatac ta                                               502

<210> SEQ ID NO 6
<211> LENGTH: 261
<212> TYPE: DNA
<213> ORGANISM: Triticum aestivum
```

-continued

<400> SEQUENCE: 6

```
atagaacatc acactcttaa gacgtaatat ttctttgaga ttttattttt gaaacttcgc      60
ctgaagggtg ctgatgtgcc cgctattcat ctaggagact aggaaaatat atgcaaaaaa     120
attcatacat atttaaaaat gataaatatg tatagagaaa atgtttatca actatagaaa     180
aatatatgca aaaatataa atatgtatga attttttttag caagtattta aatctagcat     240
ttgaaagaaa aataaacaag t                                               261
```

<210> SEQ ID NO 7
<211> LENGTH: 327
<212> TYPE: DNA
<213> ORGANISM: Triticum aestivum

<400> SEQUENCE: 7

```
attagaaaaa tgttaaacgt gtatagaaaa atgttaccat gtaattaaaa attgtataaa      60
attatcatgt attttaaaa aataaccaa gcatttaaaa acaatatttt aaaaatgtta     120
ataaggatt tgaaaaattc taaacgtgta tacaaaaatg ttgaccatgt attaaaaaat     180
gttaatcttg tatttaaaaa tgtaatcaag catttagaaa aacagttaaa ttgtatagaa     240
atgtacccag aaaatcttga tattatattt caaaaatgta atcaagcatt tgaaaaatat     300
tttaaaaatg tgtatagaaa aaatgtt                                          327
```

<210> SEQ ID NO 8
<211> LENGTH: 236
<212> TYPE: DNA
<213> ORGANISM: Triticum aestivum

<400> SEQUENCE: 8

```
aaccatgtat ttaaaaaatt ttaaacttgt atttgaaaca tgttaatcat gtattagata      60
tataccaaat atgtatgtaa aataacaatg aaaatccaag ggaaacgaaa gaaaaacaaa     120
tgaaaacggg aaaaaaacaa aaaatgaagg aaaaaaaaga aaaaacattg aaaaccaaga     180
aagaaacaaa gagaaccgga gaataacaaa caaaagggaa agaaaaggtg aaaaaa        236
```

<210> SEQ ID NO 9
<211> LENGTH: 504
<212> TYPE: DNA
<213> ORGANISM: Artificial Sequence
<220> FEATURE:
<223> OTHER INFORMATION: promoter

<400> SEQUENCE: 9

```
ctagtaaaaa caagaaacaa agaaaaaagg atgacaaaca aggaaaaaaa ttaaaaatcc      60
ggaaaggcaa cggtaagacg actcttttcc ttcaagttgg tagcgcccta ccagggtaac     120
acgaacttga cgatgacttt atggctagga gagctacgct ggaacgagga gatccggacc     180
aaaccatgtg cgctacaaaa gtgtattatt attttttgca aaaatgatcc gaatctatta     240
tcaaaattca gcgaaataca aaacatctcg aacataatga acaatacatt gagattccag     300
gaccccaaac aaccactact gccgcgaaga aaaaggatt gggaggacag aaattatcct     360
aaccacgttc gtcctcggtt gttggtctca tcgcgcgcta acaacctgg acaacagaaa     420
aggcaaagca gtgtcctccg ctccgcagca aagaagacaa atcgtcactt gtcagaggcc     480
gtcacccaag caagcaaact gcaa                                             504
```

<210> SEQ ID NO 10
<211> LENGTH: 441

<212> TYPE: DNA
<213> ORGANISM: Artificial Sequence
<220> FEATURE:
<223> OTHER INFORMATION: promoter

<400> SEQUENCE: 10
agcttgttcg tttggtttat cccgtagtac gcgccaacgc atgtgccgca ccgcgtttgc    60
ggtggagagc gcaggcatgc atcaaccaac aaacgaaaca gtgcagttgc ttacagtgct   120
ccatccctcc aaaaaaaaaa gttgcagtgc tctatctatc tatctacaca atcaacgcgg   180
gcctcctgct ccttcgccgc aagccccgtt ccgtcctcag tcttcacgtg gattctgcaa   240
cctccttcca gcagcttgtc accacggacg cttcctcgtg cgctgctcgc gtggcaccgg   300
ccccgctttc cagcgtgctc cgcgcgggcc gcggccgcaa atcgcagacc caacacgcca   360
cccgccaggg ggccgttcgt acgtacccgc ccctcgtgta aagccgccgc cgtcgtcgcc   420
gtcccccgct cgcggccatt t                                             441

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
ctgctggaca ggatatggaa                                                20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
tcgcgctgca gggcctcctt                                                20

<210> SEQ ID NO 13
<211> LENGTH: 21
<212> TYPE: DNA
<213> ORGANISM: Artificial Sequence
<220> FEATURE:
<223> OTHER INFORMATION: primer

<400> SEQUENCE: 13
tcacgtggat tctgcaacct c                                              21

<210> SEQ ID NO 14
<211> LENGTH: 28
<212> TYPE: DNA
<213> ORGANISM: Artificial Sequence
<220> FEATURE:
<223> OTHER INFORMATION: primer

<400> SEQUENCE: 14
caggacggac catggcggcg gccgggat                                       28

<210> SEQ ID NO 15
<211> LENGTH: 29
<212> TYPE: DNA
<213> ORGANISM: Artificial Sequence
<220> FEATURE:
<223> OTHER INFORMATION: primer

```
<400> SEQUENCE: 15
cgccgccatg gtccgtcctg tagaaaccc                                          29

<210> SEQ ID NO 16
<211> LENGTH: 21
<212> TYPE: DNA
<213> ORGANISM: Artificial Sequence
<220> FEATURE:
<223> OTHER INFORMATION: primer

<400> SEQUENCE: 16
gtgatgtcag cgttgaactg c                                                  21

<210> SEQ ID NO 17
<211> LENGTH: 20
<212> TYPE: DNA
<213> ORGANISM: Triticum aestivum

<400> SEQUENCE: 17
aaaaatgtaa tcaagcattt                                                    20

<210> SEQ ID NO 18
<211> LENGTH: 10
<212> TYPE: DNA
<213> ORGANISM: Triticum aestivum

<400> SEQUENCE: 18
cccggccgcc                                                               10
```